US00PP09555P

United States Patent [19]

Morrison

[11] Patent Number: Plant 9,555

[45] Date of Patent: May 21, 1996

[54] HIBISCUS PLANT NAMED 'PINK WONDER'

[76] Inventor: William L. Morrison, 1023 W. Crescent Ave., Park Ridge, Ill. 60068

[21] Appl. No.: 434,587

[22] Filed: May 1, 1995

[51] Int. Cl.[6] ..... A01H 5/00

[52] U.S. Cl. ..... Plt./67.8

[58] Field of Search ..... Plt./67.8

[56] References Cited

U.S. PATENT DOCUMENTS

P.P. 9,311 10/1995 Bost ..... Plt./67.8

*Primary Examiner*—James R. Feyrer

[57] ABSTRACT

This invention is a new and distinct winter hardy Hibiscus plant cultivar named 'Pink Wonder' resulting from a definite effort over 14 years by selection and hybridization that produces a very large brilliant pink flower of elegant form and substance on a plant which has many landscape applications blooming profusely from midsummer to frost with flowers that maintain their shape for two to four days each.

2 Drawing Sheets

BACKGROUND OF THE NEW PLANT

The objective of this breeding program was to develop a plant with the following characteristics:

(a) Exceptionally large bright pink flowers, relatively flat, with overlapping petals that have numerous ripples.

(b) A plant of medium size with good form and habit for use in various landscape plantings that in winter hardy when left outside in freezing temperatures during the winter.

(c) Each extra large flower remains open and flat for two to four days.

(d) A blooming cycle period from midsummer to frost.

This new plant was developed over a period of 14 years by cross pollinating parent plants which have many desirable characteristics. The last hybridization to create 'Pink Wonder' was made by taking a heavy application of pollen from 'Bill's Giant' (a very large mostly white hibiscus flower) to 'Nova' (a red, white and pink hibiscus flower) in the summer of 1991. The seed from this 'Nova' parent first bloomed in 1992. The ancestry of the parents include *Hibiscus moscheutos, Hibiscus militaris,* and *Hibiscus palustris.*

We have asexually reproduced this plant by root crown division and tip cuttings and the new plants produce the exact same characteristics of the 'Pink Wonder' that first bloomed in 1992. This hybridization and sexual reproduction was done in Park Ridge, Ill.

DESCRIPTION OF THE DRAWINGS

The accompanying photographs depict the flower color and foliage color of 'Pink Wonder' as true as can be reasonably done by conventional photographic procedures.

In the drawing:

Sheet 1 shows one flower of the plant with a 3 inch by 5 inch file card positioned next to the flower to reflect the size, attitude, color and character of the blossom when fully open. This photograph shows the full appearance of the flower, the high degree of imbrication of adjacent petals as well as the petal margin and rippled appearance characteristic of the petals.

Sheet 2 of the drawing shows a typical mature, simple leaf of this plant with the leaf petiole. This photograph illustrates the venation, leaf shape, the serrated nature of the margin, and the relative size and color of the leaf stem. Note that the leaf petiole may be blushed with red.

DESCRIPTION OF THE NEW PLANT

The following is a detailed description of this new variety, color terminology is in accordance with *The Royal Horticultural Society Colour Chart* (indicated by the initials R.H.S. plus number).

THE PLANT

Type: Tender, herbaceous perennial.

Classification: Hybrid variety Hibiscus.

Origin: Seedling.

Parentage:

*Seed parent.*—Hibiscus 'Nova'.

*Pollen parent.*—Hibiscus 'Bill's Giant'.

Propagation: Reproduces the exact same characteristics by root crown division and by tip cuttings as 'Pink Wonder'.

Form: Numerous stalks grow upright each year from perennial roots.

Habit: Individual upright stalks with many leaves uniformly distributed on the stalks and numerous flowers bloom continuously one after another at the top of the plant. Rapid and strong stalk growth have flowers outward while blooming.

Productivity: Produces continuous new flower displays.

Precocity: Elegant display of flowers one after another at the top of the stalk.

Stalks: Strong and smooth skin covered that hold many leaves and flowers securely.

Resistance to disease: We have not had any rust, black spot, or fungus develop so no foliage sprays have been necessary. This plant does not attract slugs.

Moisture requirements: This plant survives droughts without watering.

Temperature: On 100 degree days the flowers bloom as if it were a mild day.

Rain: The plants can stand in heavy rain water without any adverse effects.

Insects: We have had negligible insect damage without using any pesticide sprays.

Animals: Rodents; rabbits and squirrels, do not bother the roots.

Rooting: The plants root easily and we have not used fertilizer.

Foliage: Good sized leaves evenly distributed vertically and horizontally on the stalks.

Leaves: Abundant and decorative in alternate order:

*Margins.*—Lengths of four to seven inches.

*Color.*—Dark green (approxiamtely R. H. S. 137A).

*Petiole.*—Two to three inches. Lenticels — none.

*Form.*—Elongated heart.

*Stipules.*—None.

Stem color: Lighter green than the leaves (R. H. S. 137A).

Height: Four and one half feet to six feet.

Weed control: The white hair roots spread our from the succulent roots and reduce weeds in the root area so there is less weeding and cultivating required.

Dormancy: Remains dormant during the winter.

THE FLOWER

Date described: Aug. 25, 1994.

Bud: Shaped like a pointed egg, and egg size one to two days before blooming.

Blooming habit: Continuous and free blooming.

Petals:

*Length.*—Five to six inches.

Diameter of flower: 10 to 12 inches.

Shape: Almost circular, relatively flat with five lightly rippled overlapping petals.

Filaments:

Color.—Very light pink.

Stamens: Very numerous.

Pistil: Two to three inches.

Stigma:

*Color.*—Rose red.

Style:

*Color.*—Rose red near stigma and white supporting the stamens.

Pollen:

*Color.*—White, tinged with yellow.

Shape of petals: Fully overlapping and broadly obovate (almost reniform) recurved at base to form a small green star of revealed calyx, with overall circular shape.

Aspect of flower: Central one-fourth — satiny; outer three-fourths — velvety.

Texture: Fine kidskin-like appearance and strongly self supporting.

Color of flower: Small satiny rose red center comprising about one-fifth of each petal blending with the four-fifths majority of the petals that have a bright pink (approximately R.H.S. 64C) color with numerous light rose red veins in each petal. The pink color of the petals is much stronger that the R.H.S. chart shows.

Calyx: Five tooth with medium green color (not as dark as the leaves.)

Bractlets: Medium green (lighter than the leaf color.)

Flowers: Numerous flowers on each stalk with essentially flat appearance.

Blooming period: Mid summer to frost with continuous color presentation with each flower lasting two to four days.

Peduncle:

*Length.*—3 to 5 inches and stiff to support the flower during blooming and the seed pod formation later.

I claim:

1. A spectacular new and distinctive cultivar of winter hardy hibiscus substantially as herein shown and described that can be left outside over the winter in freezing temperatures with exceptionally large bright pink flowers of elegant form and substance on a plant of great landscape value blooming continuously from mid-summer to frost with the individual flowers holding their shape two to four days.

* * * * *

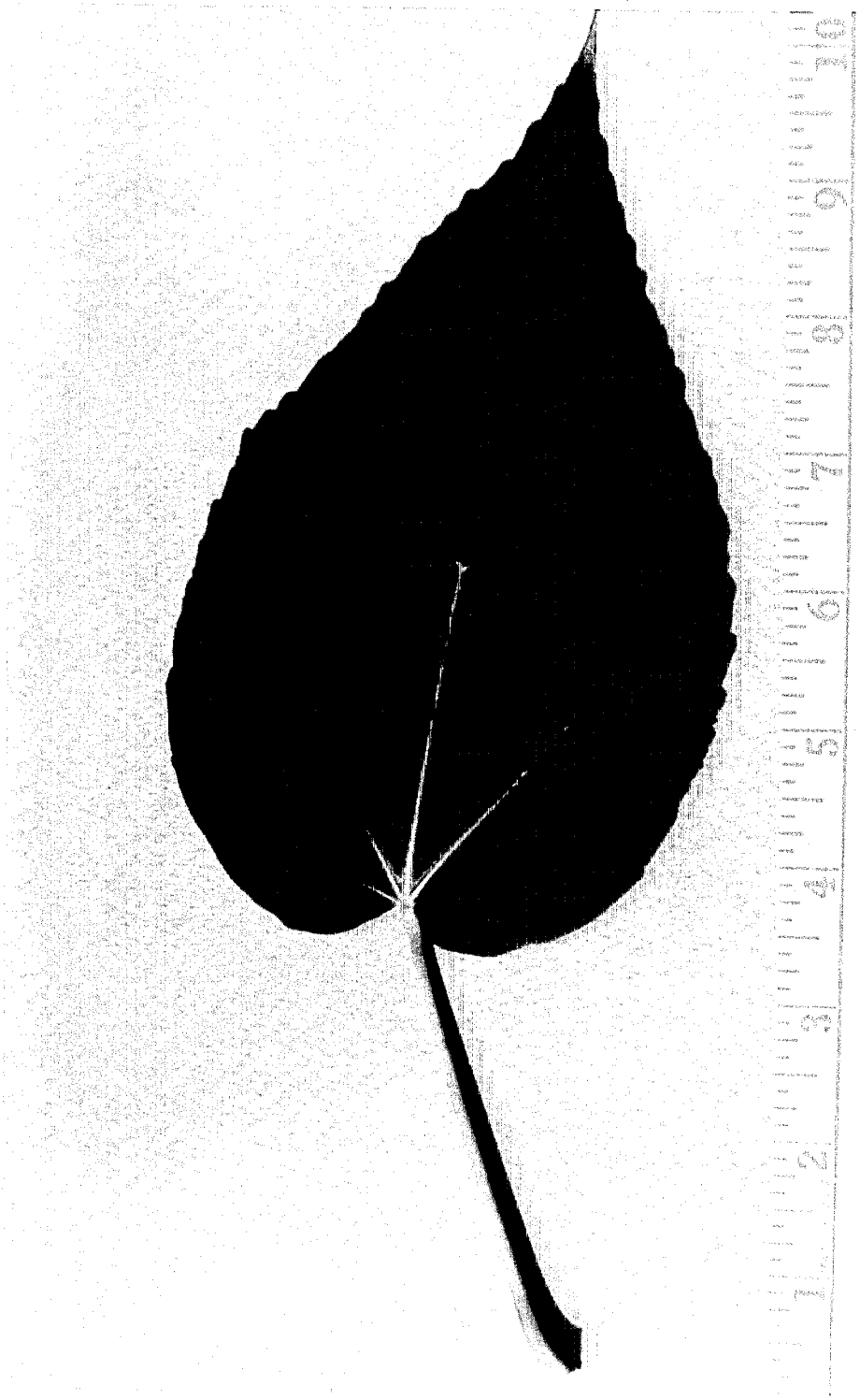

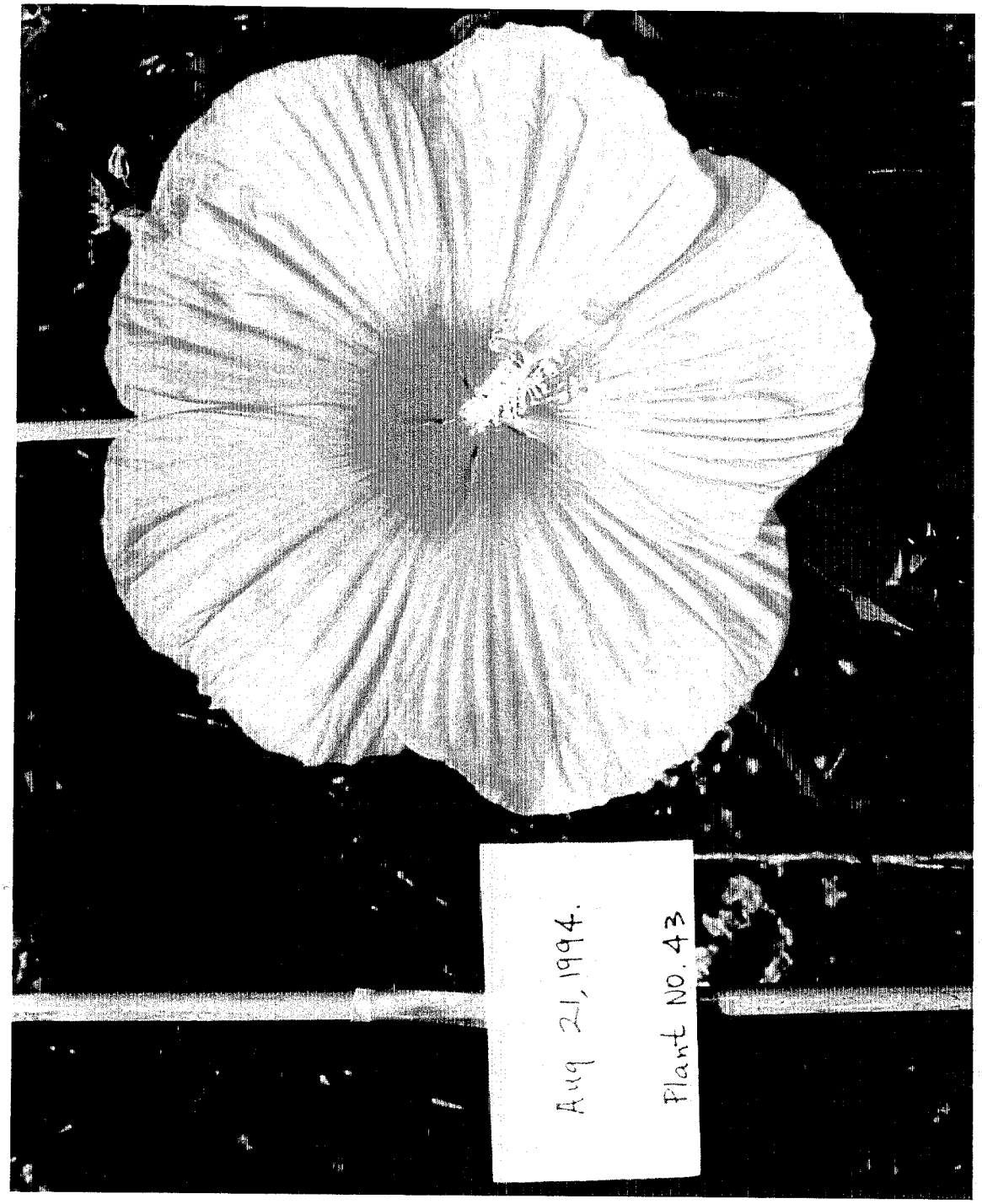
Aug 21, 1994.
Plant No. 43